United States Patent [19]

Chin

[11] Patent Number: 4,863,440

[45] Date of Patent: Sep. 5, 1989

[54] PRESSURIZED MANUAL ADVANCEMENT DILATATION CATHETER

[75] Inventor: Albert K. Chin, Palo Alto, Calif.

[73] Assignee: Thomas J. Fogarty, Palo Alto, Calif.

[21] Appl. No.: 812,384

[22] Filed: Dec. 23, 1985

[51] Int. Cl.$^4$ .............................................. A61M 5/00
[52] U.S. Cl. .................................... 604/271; 128/344
[58] Field of Search ......................... 604/271; 128/344

[56] References Cited

U.S. PATENT DOCUMENTS

| 3,050,060 | 8/1962 | Hoffman | 604/271 |
| 3,421,509 | 1/1969 | Fiore | 604/271 |
| 4,243,040 | 1/1981 | Beecher | 604/271 |
| 4,271,839 | 6/1981 | Fogarty et al. | 128/344 |
| 4,315,512 | 2/1982 | Fogarty | 128/344 |
| 4,318,410 | 3/1982 | Chin | 604/271 |
| 4,493,711 | 1/1985 | Chin et al. | 604/271 |

OTHER PUBLICATIONS

"Toposcopy–Frictionless Method of Entering Body Cavities and Tracts", Zeimer et al., New York State Journal of Medicine, Jul. 15, 1966, pp. 1925-1930.

*Primary Examiner*—C. Fred Rosenbaum
*Assistant Examiner*—K. Daley
*Attorney, Agent, or Firm*—Limbach, Limbach & Sutton

[57] ABSTRACT

The subject invention relates to a method and apparatus particularly suitable for use in dilating occluded blood vessels. The apparatus includes a tubular catheter having a balloon member connected to the distal end thereof. The balloon is initially located in an inverted manner with the free end thereof being connected to a reinversion member. A tubular sheath is telescopically mounted within the catheter surrounding said balloon member. In operation, the balloon member is everted by sliding the sheath beyond the distal end of the catheter. Fluid pressure can be utilized to facilitate eversion and to laterally expand the balloon member after it has been extruded through the occlusion. The sheath also aids in reinverting the balloon member.

14 Claims, 1 Drawing Sheet

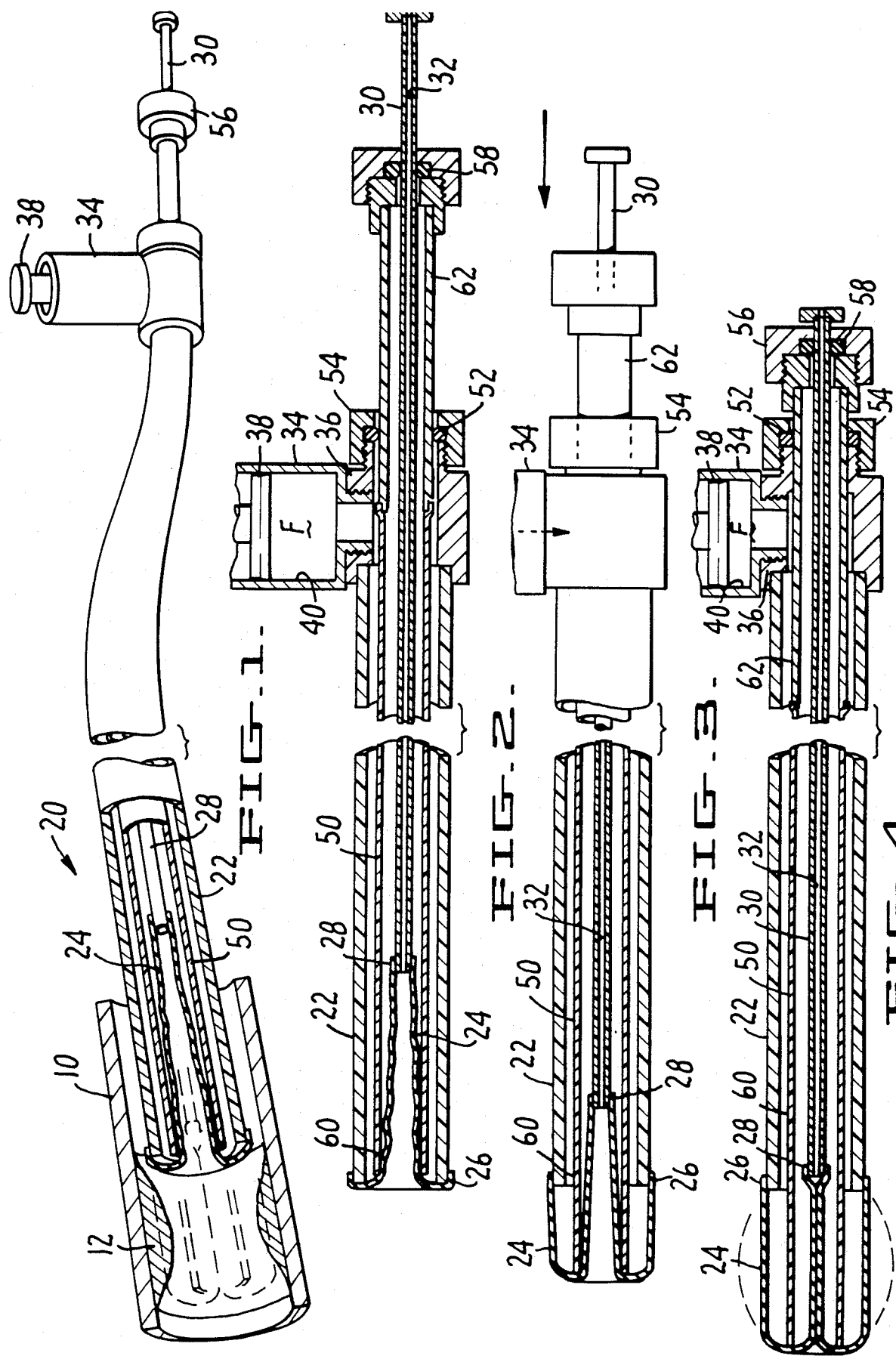

PRESSURIZED MANUAL ADVANCEMENT DILATATION CATHETER

TECHNICAL FIELD

The subject invention relates to a method and apparatus suitable for use in dilating occluded blood vessels. The invention is particularly concerned with such a method and apparatus wherein dilation is achieved through means of a balloon member which is initially inverted within the distal end of a catheter and is thereafter extruded through and expanded within the occlusion being treated. The invention is intended for use in treating either arterial or venous occlusions.

BACKGROUND OF THE INVENTION

In the prior art, a number of techniques have been developed for treating occluded blood vessels. One type of treatment is to surgically attach unblocked vessels to bypass the occlusion. Another surgical approach is to remove the occlusion from within the vessel. More recently, dilatation catheter devices have been developed which can be inserted into the blood vessel having an occlusion.

One type of dilatation catheter can be found in U.S. Pat. No. 4,271,839, issued June 9, 1981, and assigned to the same assignee as the subject invention. In this device, an elastic balloon element is sealingly attached to the distal end of a catheter. The balloon element is held in an inverted condition within the catheter. In use, the catheter is brought into position adjacent the occlusion. The balloon element is everted from the catheter through the occlusion by applying fluid pressure to the interior of the catheter. The balloon is extruded through the occlusion in anisotropic fashion, that is, in advance of substantial lateral expansion of the balloon. Once the balloon is in place within the occluded section of the vessel, continued fluid pressure is applied to laterally expand the balloon and dilate the occlusion. When the occlusion has been treated, the fluid pressure is released causing the balloon to collapse. A cord connected to the free end of the balloon is then retracted to reinvert the balloon within the catheter prior to removal of the catheter from the blood vessel.

The particular dilatation catheter discussed above has many important advantages. For example, it has been found to be highly beneficial to have a balloon member in an initially inverted condition and to extrude that balloon member through the occlusion. This linear rolling extrusion method produces very little friction between the balloon member and the occluded vessel wall. The catheter of the subject disclosure is intended to provide the advantages of the catheter described in U.S. Pat. No. 4,271,838, and to provide additional improvements thereto as discussed below.

As pointed out above, prior art inverted balloon dilatation catheters have extruded the balloon member used therein under fluid pressure. In use, the balloon member tends to advance with initial, abrupt and uncontrolled motions. Relatively high pressures are required to begin the extrusion process when the balloon is completely inverted. As the balloon begins the eversion process, lower pressures are required. The requirement to change the pressure occurs quite rapidly and is therefore difficult for the catheter operator to adjust.

Another difficulty with the prior art dilatation catheters concerns the different pressure requirements needed to extrude the balloon member through a stenosis and the dilation process itself. The pressure required to overcome the frictional forces between the balloon member and the catheter during the extrusion process is quite high compared to the pressures required for the dilation process and assumes a significant portion of the total inflation pressure. It would be desirable to reduce the amount of fluid pressure needed to extrude the balloon, reserving that pressure more for dilation.

As discussed above, in prior art evertable catheters, means is provided for reinverting the balloon member prior to retraction of the catheter from the blood vessel. It was found desirable to reinvert the balloon member to reduce friction between the balloon member and the blood vessel wall during retraction. It is also desirable in that it enables the balloon element to be used for the serial treatment of multiple occlusions within a vessel, with reinversion occurring before each serial dilation. Because the balloon member is sometimes quite long compared to the diameter of the catheter, folds of the depressurized elastic balloon member often became bunched up around the mouth of the catheter during the reinversion process. The cluster of folds at the end of the catheter can actually result in an increase in the effective diameter of the catheter and thereby increase friction. Accordingly, it would be desirable to provide a catheter which reduces the likelihood of the balloon bunching up near the distal end of the catheter during reinversion.

Accordingly, it is an object of the subject invention to provide a new and improved method and apparatus for dilating occluded blood vessels.

It is another object of the subject invention to provide a new and improved method for manually extruding a balloon element into a body passage.

It is a further object of the subject invention to provide a new and improved method for combining a manual technique with a pressurized eversion to extrude a balloon member.

It is another object of the subject invention to provide a new and improved method of reinverting a balloon member without bunching.

It is still a further object of the subject invention to provide an improved new and improved apparatus for extruding a balloon member into a body passage.

It is still another object of the subject invention to provide a catheter which can extrude a balloon member in a gentle, even manner, avoiding abrupt movements.

It is still a further object of the subject invention to provide a new and improved catheter having enhanced dilation capabilities.

It is still another object of the subject invention to provide a new and improved catheter where the difference between the pressure required to extrude the balloon and and the pressure required to produce dilation is reduced thereby reducing the chance of balloon breakage.

SUMMARY OF THE INVENTION

In accordance with these and other objects, the subject invention provides for a new and improved method and apparatus for dilating blood vessels. The apparatus includes an elongated, flexible, tubular catheter having distal and proximal ends. A balloon member is provided having a mouth peripherally sealed to the distal end of the catheter. In the preferred embodiment, the free end of the balloon member is connected to a reinversion tube or wire which projects out of the proximal end of the catheter.

In accordance with the subject invention, the catheter is also provided with an internal tubular sheath which is mounted within the tubular catheter and around the balloon member and reinversion tube or wire. During the extrusion process, the sheath is pushed out of the distal end of the catheter, facilitating the extrusion of the balloon member.

Preferably, the catheter is pressurized during eversion such that the sheath is automatically preceded by the unrolling front of the everted balloon. Even in the case where the catheter is pressurized, the manual movement of the sheath significantly aids the forward translation of the balloon such that a large portion of the the inflation pressure is reserved for dilation rather than extrusion. In this manner, the incidence of balloon rupture is decreased. The manual translation of the sheath also tends to provide a smoother, more even extrusion thereby avoiding abrupt movements and reducing the likelihood of damage to the blood vessels.

The sheath also provides for added column strength. More particularly, in some instances, where stiffer arteriosclerotic lesions are encountered, a dilating element of higher column strength may be desired. The flexible sheath imparts this column strength to the dilating balloon, without loss of the attractive properties of a simple linear extrusion catheter.

When the dilation process is complete, the balloon member is reinverted by retracting the reinversion tube. During this process, the balloon member continuously engages the sheath creating a bearing force that tends to simultaneously retract the sheath. In this manner, the reinverting balloon is always biased against the retreating distal end of the sheath such that the balloon member will not bunch up.

Further objects and advantages of the subject invention will become apparent from the more detailed description taken in conjunction with the drawings in which:

BRIEF DESCRIPTION OF THE DRAWINGS

FIG. 1 is a perspective view, partially in section, illustrating an occluded blood vessel in the process of being treated by the method and apparatus of the subject invention.

FIG. 2 is a cross-sectional view illustrating the catheter of the subject invention.

FIG. 3 is a cross-sectional view similar to FIG. 2 illustrating the initial step of extruding the balloon member from the catheter.

FIG. 4 is a cross-sectional view similar to FIG. 3, illustrating the fully extruded balloon member.

DETAILED DESCRIPTION OF THE PREFERRED EMBODIMENT

FIG. 1 illustrates the apparatus 20 of the subject invention, treating an occluded blood vessel 10. Blood vessel 10 is shown with an occlusion 12. The occlusion 12 is typically known as arteriosclerotic plaque or atheroma. The apparatus and method of the subject invention is particularly suitable for treating this type of occlusion. It should be understood, however, that the invention is also applicable for other types of occlusions, such as fibromuscular dysplasia in veins.

The principal elements of the subject apparatus 20 include a flexible catheter 22 that is generally tubular in construction and fabricated from an inert polymer material, such as Dacron. A balloon member 24 is provided which is preferably fabricated of a highly flexible generally inelastic material, such as vinyl plastic. Balloon 24 has a peripheral mouth 26, which is secured to the distal end of the catheter 22. In the initial position of the apparatus, the free end 28 of the balloon member is inverted within the body of the catheter.

Connected to the free end of the balloon member 28 is a reinversion tube 30 having a central bore 32. Reinversion tube 30 extends out the proximal end of the catheter. While the balloon and reinversion member 30 are shown as two elements, it is possible to use a single integral tube with one end being formed as the balloon. It is also possible that a wire or cord may be substituted for the tube 30. The use of a tube is desirable, however, since it permits the introduction of pressure monitoring equipment and can accommodate a guide wire. Drugs or contrast liquids can be injected via the bore 32 in reinversion tube 30.

A means for pressurizing the interior of the catheter is provided. In the illustrated embodiment, this means is provided by a simple syringe 34 connected to the catheter by a coupling 36. Syringe 34 includes a slidable piston 38 for compressing a fluid F within cylinder 40. The means for pressuring the interior of the catheter may additionally include pressure measuring and maintaining mechanisms, such as those embodied in "The Indeflator", manufactured by Advanced Cardiovascular Systems, Inc.

In accordance with the subject invention, a means is provided to assist in the manual extrusion of balloon member 24. This means is defined by an elongated tubular sheath 50. Sheath 50 is telescopically mounted for slidable movement within the tubular catheter 22 and about the balloon member and reinversion tube 30. The outer surface of the tubular sheath 50 is sealingly engaged with the proximal end of the tubular catheter through an 0-ring seal 52. The 0-ring seal can be tightened with a screw cap 54. The distal end of the sheath is also sealed utilizing a cap 56 and an O-ring 58 disposed about the circumference of the reinversion tube 30. By this arrangement, tube 30 can be moved relative to the sheath while maintaining a fluid-tight seal.

In a preferred embodiment, flexible sheath 50 is formed in two parts. The distal end 60 may be formed of a flexible material, such as plastic to facilitate movement in the blood vessel. In the alternative, a tightly coiled metal spring, or metal spring covered by plastic could be utilized to form the distal end 60. The proximal end of the sheath 62 is formed from a rigid material, such as metal, hard plastic or metal reinforced plastic. It is desirable to form the distal end of a more rigid material to ensure that the fluid seal is maintained about 0-ring 52.

Having described the structure of the subject device, its operation will now be discussed. Initially, an incision is made in the blood vessel 10 on one side of the occlusion 12 to be treated. The distal end of the catheter 20 is then introduced into the vessel through the incision. The catheter is then fed through the blood vessel to a position such that the distal end of the catheter is adjacent the occlusion. At this point, the balloon member 24 is extruded out from the catheter into the occluded area.

In the prior art discussed above, the extrusion step was performed simply by applying fluid pressure to the interior of the catheter. Unless the pressure was accurately controlled, this approach often caused the balloon to evert in abrupt fashion because of the pressure requirements for everting the balloon out of the catheter and extruding it through the occlusion are quite different. Smooth eversion is facilitated using the method and apparatus of the subject invention.

With the present invention, smooth eversion of the balloon member is achieved by sliding the sheath 50 in the direction indicated by arrow A in FIG. 3. The distal end of the sheath 50 tends to move and force the balloon member out from within the catheter and extrude it through the occlusion. As shown in FIG. 4, the sheath can be fully extended to completely evert the balloon member. At that time, fluid pressure from syringe 34 is used to inflate the balloon and dilate the blood vessel.

In a preferred method of the subject invention, the balloon 24 is extruded with a combination of the manual pressure provided by the sheath 50 and fluid pressure provided by syringe 34. Providing some fluid pressure during extrusion results in the sheath being automatically preceded by the unrolling front of the everting balloon. In this manner, the advantages of a relatively frictionless, pressurized linear extrusion is preserved.

Another advantage provided by the subject apparatus is that the flexible sheath can provide added column strength to the balloon member. More particularly, the balloon member may be pushed through relatively stiff lesions without merely having to rely on fluid pressure. A further advantage of the subject method and apparatus is that much of the fluid pressure normally used to evert the balloon is reserved for dilating the balloon. Since the fluid pressure needed to extrude the balloon is less than in the prior art, the risk of balloon rupture will be decreased.

It should be noted that the balloon can be extruded with a combination of fluid pressure and movement of reinversion tube 30 (in the direction of arrow A). The latter approach may be suitable in situations where it is undesirable to manually evert the balloon with the sheath. Even if the sheath is not used to aid extrusion, it may still be used to facilitate reinversion of the balloon as discussed immediately below.

After the occlusion has been dilated, the catheter is removed. Prior to its removal, the fluid pressure is reduced, deflating the balloon member. Preferably, the balloon member is reinverted within the catheter prior to its removal from the vessel.

In accordance with the subject invention, this reinversion is performed by retracting tube 30 in a direction opposite to arrow A in FIG. 3. As in the prior art, this action will tend to draw the balloon back within the catheter. Unlike the prior art, the balloon member of the subject invention is continually engaged with the end of the sheath. As the balloon is reinverted, the pressure of the balloon on the sheath causes the sheath to retract within the catheter. Using this approach, there are no loose folds of balloon material extending beyond the distal end of the catheter sheath combination.

Once the balloon has been fully reinverted, the catheter can easily be slipped out of the blood vessel, or progressively moved through the vessel for the treatment of additional occlusions. As pointed out above, the slidable sheath can be used to aid reinversion of the balloon even if the sheath had not been used to extrude the balloon member initially. More particularly, if the balloon is extruded either through the use of pressure alone, as in the prior art, or utilizing the reinversion tube, the flexible sheath can then be slid into the fully extruded balloon prior to reinversion.

In summary, there has been provided a new and improved method and apparatus for dilating occluded blood vessels. The method and apparatus utilizes an internal sheath to combine the advantages of both pressure and manual eversion techniques to extrude a balloon member from within a catheter out and through an occlusion. The sheath also facilitates reinversion of the balloon.

While the subject invention has been described with reference to a preferred embodiment, it is to be understood that changes and modifications could be made thereto by one skilled in the art without varying from the scope and spirit of the subject invention as defined by the appended claims.

I claim:

1. A method of manually everting a balloon member from within a tubular catheter, said balloon member having a mouth peripherally sealed to one end of said catheter, said method comprising the steps of:
   providing an internal tubular sheath telescopically mounted within said tubular catheter and around the balloon member;
   sliding said sheath within said catheter toward said one end thereof, thereby applying manual pressure to said balloon member;
   applying fluid pressure internally of the catheter during the step of applying manual pressure to the balloon member to simultaneously subject the balloon member to internal manual and fluid pressure and evert the member out of the catheter.

2. A method as recited in claim 1 wherein said fluid pressure is applied after the balloon member has been everted to laterally expand said balloon member.

3. A method as recited in claim 1 further comprising reinverting the balloon member into the catheter after eversion by providing an elongated reinverting member within said sheath, with one end of said reinverting member being connected to the free end of said balloon member, and retracting said reinverting member to draw said balloon member into the catheter while contact is maintained between said sheath and said balloon member and internal fluid pressure is relieved from the catheter.

4. A linear extrusion apparatus comprising:
   an elongated tubular catheter having distal and proximal ends;
   a balloon member having a mouth peripherally sealed to the distal end of the catheter, said balloon member being inverted within the tubular catheter;
   an internal tubular sheath telescopingly received within said catheter and around said inverted balloon member, said tubular sheath being slidable within said catheter towards the distal end thereof to engage and manually evert said balloon member; and
   means for pressurizing the interior of said catheter to subject said balloon member to internal fluid pressure simultaneously with the engagement thereof by the sheath and cause the lateral expansion of said balloon member after it has been everted.

5. An apparatus as recited in claim 4 wherein said means for pressurizing said catheter includes a means for sealing the proximal end of said sheath and for sealing the proximal end of said catheter with respect to said sheath.

6. An apparatus as recited in claim 5 wherein the distal end of said sheath is formed from a flexible material and the proximal end of said sheath is formed of a material which is relatively rigid as compared to the distal end.

7. An apparatus as recited in claim 4 further comprising an elongated reinversion member telescopingly extending through said sheath and connected to the free end of said inverted balloon member such that after said balloon member is everted, the reinversion member can be retracted, causing said balloon member to reinvert while contact is maintained between said sheath and said balloon member.

8. An apparatus as recited in claim 7 wherein said reinversion member comprises a tube sealingly secured to and opening through said balloon member.

9. An apparatus for dilating a partially occluded section of a blood vessel, said apparatus comprising:
   an elongated tubular catheter having distal and proximal ends;
   a balloon member having a mouth peripherally sealed to the distal end of said catheter, said balloon member being inverted within said tubular catheter;
   means for pressurizing the interior of said catheter to subject the balloon member to fluid pressure; and
   an internal tubular sheath having distal and proximal ends, said tubular sheath being telescopingly received within said catheter and around said inverted balloon member such that the eversion of said balloon member can be manually assisted by sliding the distal end of the sheath into engagement with the balloon member and past the distal end of the catheter simultaneously with the pressurizing of the interior of said catheter and wherein said means for pressurizing the interior of said catheter is adapted to laterally expand said balloon member after it has been everted from the catheter.

10. An apparatus as recited in claim 9 wherein said means for pressurizing said catheter includes a means for sealing the proximal end of said sheath and for sealing the proximal end of said catheter with respect to said sheath.

11. An apparatus as recited in claim 9 wherein the distal end of said sheath is formed from a flexible material and the proximal end of said sheath is formed of a material which is relatively rigid as compared to the distal end.

12. An apparatus as recited in claim 9 further comprising an elongated reinversion member telescopingly extending through said sheath and connected to the free end of said inverted balloon member such that after said balloon member is everted, the reinversion member can be retracted, causing said balloon member to reinvert while contact is maintained between said sheath and said balloon member.

13. An apparatus as recited in claim 12 wherein said reinversion member comprises a tube sealingly secured to and opening through said balloon member.

14. In a dilatation catheter having a balloon member with a mouth peripherally sealed at the distal end of the catheter and an elongated reinverting member extending through the catheter and connected to the free end of the balloon member, an improved method for inverting the balloon member within the catheter, said method comprising:
   providing a tubular sheath within said catheter and about said reinverting member;
   sliding said sheath beyond said distal end of said catheter; and
   retracting said reinverting member to bring said balloon member into contact with said sheath to draw said sheath into the catheter while inverting said balloon member.

* * * * *